United States Patent [19]

Johnson et al.

[11] 4,034,082

[45] July 5, 1977

[54] METHOD TO PREVENT REPRODUCTION IN WARM-BLOODED FEMALE ANIMALS WITH NONAPEPTIDES

[75] Inventors: Edwin Samuel Johnson, Antioch; Wilfrid Francis White, Arlington Heights, both of Ill.

[73] Assignee: Abbott Laboratories, North Chicago, Ill.

[22] Filed: Mar. 1, 1976

[21] Appl. No.: 662,759

[52] U.S. Cl. .................... 424/177; 260/112.5 LH; 424/359; 424/361
[51] Int. Cl.$^2$ .................................. A61K 37/02
[58] Field of Search .......... 424/177; 260/112.5 LH

[56] References Cited

UNITED STATES PATENTS

| | | | |
|---|---|---|---|
| 3,784,535 | 1/1974 | Flouret | 260/112.5 LH |
| 3,853,837 | 12/1974 | Fujino et al. | 260/112.5 LH |
| 3,880,825 | 4/1975 | Sakakibara et al. | 424/177 X |
| 3,886,135 | 5/1975 | McKinley et al. | 424/177 X |
| 3,886,137 | 5/1975 | Yardley | 424/177 X |
| 3,888,838 | 6/1975 | Immer et al. | 424/177 X |
| 3,890,437 | 6/1975 | Foell et al. | 424/177 |
| 3,892,723 | 7/1975 | McKinley et al. | 424/177 X |
| 3,914,412 | 10/1975 | Gendrich et al. | 424/177 |
| 3,915,947 | 10/1975 | Shields | 424/177 X |
| 3,917,825 | 11/1975 | Matsuzawa et al. | 424/177 |

OTHER PUBLICATIONS

Greenstein et al., Chemistry of the Amino Acids, vol. 2, John Wiley & Sons, Inc., New York, (1961), pp. 768–769.

Primary Examiner—Albert T. Meyers
Assistant Examiner—Vera C. Clarke
Attorney, Agent, or Firm—Paul D. Burgauer; Robert L. Niblack

[57] ABSTRACT

With the administration of 1 μg – 10mg/kg of specified nonapeptides, reproduction is prevented in warm-blooded animals of the reproductive age.

7 Claims, No Drawings

METHOD TO PREVENT REPRODUCTION IN WARM-BLOODED FEMALE ANIMALS WITH NONAPEPTIDES

DETAILED DESCRIPTION OF THE INVENTION

In the past few years, reproduction, conception and/or fertilization in warm-blooded animals has been prevented by the administration of a variety of physiologically active compositions, most of which consist of several components that occur naturally in said animals or synthetic analogs thereof. These components are, in some instances, given simultaneously and in others, are given separately at various times during a normal menstrual or ovulatory cycle. Unfortunately, some of these naturally present components or their synthetic analogs have other effects on the animals and exogenous administration thereof leads to undesirable side effects. For this reason, long-term use of such drugs is dangerous, and prevents widespread acceptance thereof.

It is therefore an object of this invention to prevent reproduction in female, warm-blooded animals in the reproductive age. It is a more specific object of this invention to provide a method to prevent reproduction of such animals by administration of an unnatural drug to said animals. It is an even more particular object of this invention to provide a method for preventing reproduction in mature female, warm-blooded animals by administration of a physiologically safe, synthetic chemical.

These and other objects are accomplished by providing a process for preventing reproduction by administering to a female, warm-blooded animal in or before reaching the reproductive age between 1 $\mu$g and 10 mg/kg./day of a nonapeptide L-pGlu-L-His-L-Trp-L-Ser-L-Tyr-X-L-Leu-L-Arg-L-Pro-NH-$C_2H_5$ wherein X denotes the optically active D-form of the divalent aminoacid moiety of tyrosine, tryptophane or phenylalanine, for at least one day in the period before said female produces one or more mature ova or after ovulation has occurred.

The term "preventing reproduction" is intended to include preventing ova to form, including premature ovulation, preventing implantation of ova after fertilization, postponing puberty or preventing embryo development. These various functions can be demonstrated in animal models; in turn, such experiments clearly show the general concept of preventing reproduction, be it by use of the nonapeptide in the follicular or luteal phase of the normal female reproductive cycle.

In a general embodiment, the above nonapeptide is administered to a cycling animal at a dose of 1 $\mu$g – 10mg/kg./day as a single daily dose or divided into 2 – 4 daily doses of the equivalent smaller amounts. If this procedure is carried out during the time span where the ovum is expected to form, ovulation will not occur because ovum development is disrupted. If the nonapeptide is administered after fertilization has taken place, implantation does not occur, and if the nonapeptide is given after implantation, the implanted ova will be expelled or the embryo will be resorbed.

In order to illustrate the process of the present invention, reference is made to the following examples which, however, are not to be construed as limiting the invention in any respect.

EXAMPLE 1

Proline carrying as a blocking group the t-butyloxycarbonyl substituent (elsewhere herein referred to as Boc-) on the amino group is esterified by combining it with a chloromethylated divinylbenzene-styrene copolymer (marketed by Bio-Rad as Merrified resin) containing 2% of cross linking, using the method described by Stewart, et al. in "SOLID PHASE PEPTIDE SYNTHESIS", (published in 1969 by Freeman & Company), San Francisco, (page 1). In this manner, a resin is produced which by hydrolysis and aminoacid analysis shows to contain 0.47 millimoles of proline/g. of resin.

In an automatic synthesizer developed according to the previously cited Merrifield apparatus, 4.6 g. of this resin/aminoacid material is used for the synthesis of the desired nonapeptide. Each N-blocked aminoacid is added in a three-fold access and allowed to couple to the existing aminoacid-resin ester in the usual coupling cycle. The coupling reaction is carried out for 4.5 hours with continuous shaking and the reaction is subsequently washed six times with methanolchloroform 1:2 for 1.5 minutes each and 4 times with ethanol for 1.5 minutes each. In each instance, a total volume of 48 milliliters is used and the drain time after shaking usually is about 1.5 minutes.

After coupling, the mixture is washed four times for 1.5 minutes each with dioxane, twice with 4N hydrochloric acid/dioxane for 5 minutes and 25 minutes, respectively, five times with dioxane for 1.5 minutes each, three times with ethanol for 3 minutes each, three times with chloroform for 1.5 minutes each, three times with 10% triethylamine/chloroform for 1.5 minutes each, four times with chloroform for 1.5 minutes each and six times with dichloromethane for 1.5 minutes each. Ordinarily the solvent used for the coupling reaction is dichloromethane or, when the solubility of the blocked aminoacid is low, a mixture of dichloromethane and dimethylformamide. Coupling is effected by the addition of a solution of dicyclohexylcarbodiimide in dichloromethane at a 2.9 fold excess.

The sequence used for deprotection, neutralization and coupling of the next aminoacid is done in a fully automatic system as described above. In this manner, the peptide is assembled using in turn Boc-Arg(Tos), Boc-Leu, Boc-D-Trp, Boc-Tyr($Cl_2$Bzl), Boc-Ser(Bzl), Boc-Trp, Boc-His(DNP), and pGlu wherein all aminoacids are in the L-form except in the case of tryptophane.

The resin is removed from the vessel and suspended in 200 ml. of 5% triethylamine/methanol and 100 ml. of distilled ethylamine is added thereto. After 24 hours, the resin is removed by filtration and the solution evaporated to yield a solid. The solid is taken up in glacial acetic acid and applied to a 3 × 50 cm. column of silica gel equilibrated with 5% methanol/chloroform.

The column is eluted with 5% methanol in chloroform until all traces of N-ethyl dinitroaniline, the yellow by-product of the histidine protecting group DNP is removed. The eluant is then changed to 33% methanol/chloroform and fractions of about 30 ml. each are collected. The compound is located by thin-layer chromatography of aliquots of the fractions (Silica gel G. 33% MeOH/$CHCl_3$, $Cl_2$/tolidine spray). The fractions containing the product are pooled and evaporated to give a solid which is precipitated from methanol with ether. This tri-protected nonapeptide (protective groups at Ser, Tyr and Arg) is thus obtained in an amount of 1.69 g., representing an overall yield of 43% of theory.

A 250 mg. sample of the above is placed in a hydrogen fluoride reaction vessel with 250 mg. of anisole and about 5 ml. of anhydrous hydrogen fluoride is distilled into it. After 1 hour at 0° C., the hydrogen fluoride is removed in vacuo, and the residue is taken up in 1% acetic acid. This solution is extracted with ether, and the aqueous phase applied to a 1 × 30 cm. column of a highly basic ion exchange resin (marketed by Bio-Rad as AG1 × 2 resin) in the acetate form. The product is eluted with 0.1 N acetic acid and localized using thin-layer chromatography (CHCl$_3$/MeOH/32% HOAc: 120/90/40, Silica gel G.,Cl$_2$/tolidine). The product bearing solution is lyophilized, rechromatographed on a Sephadex G-25 (marketed by Pharmacia of Uppsala, Sweden) column. The product eluted is collected and lyophilized to yield a fluffy white solid in a 25% overall yield.

When in the above synthesis, the Boc-D-Trp in the above sequence following the coupling with leucine (yielding Compound A) is replaced by Boc-D-Tyr(Cl$_2$B$_2$l) (yielding Compound B) or Boc-D-phenylalanine (yielding Compound C), the above synthesis proceeds in the same fashion, again in all instances, using the automatic synthesizer described above. In all instances, the nonapeptides are identified by aminoacid analysis and nmr-spectrum which confirm the presence of the assembled aminoacids in the expected molecular ratio.

EXAMPLE 2

Adult, female rats weighing an average of 200 g. were mated and then randomly divided into groups of 8 and 9 rats. In all animals, mating was determined by the presence of sperms in the vaginal opening. In all animals, subcutaneous treatment was started on day 3 of gestation and continued until day 6 with 10 $\mu$g of the above compound, b.i.d. in an aqueous vehicle containing 0.1% bovine serum albumin and 0.9% sodium chloride at a concentration of 0.02% (wt./vol.). All animals were sacrificed on day 13 and checked for toxic manifestations, fetuses or viable implants.

In the first of four groups (control), the animals received the above vehicle only. Eight of 9 animals proved pregnant. Upon sacrifice, a total of 87 implantation and 3 resorbed sites was found in the uteri.

A second group of 9 animals was treated with Compound A (X = tryptophyl). Seven of the animals showed no signs of implantation; the other two showed a total of 25 implantation sites that were all resorbed.

The third group was treated with Compound B (X = tyroslyl). Again, only 2 in 9 animals proved to have implantation; but all 22 counted sites had been resorbed. the other two showed a total of 25 implantation sites that were all resorbed.

The third group was treated with Compound B (X = tyrosyl). Again, only 2 in 9 animals proved to have implantation sites but all 22 counted sites had been resorbed.

The fourth group of 8 animals was treated with Compound C (X = phenylalanyl). Only a single resorbed implantation site was found in all the uteri upon sacrifice.

From these tests it can be seen that the compounds used in this investigation either prevent pregnancies or prevent gestation or the formation of a viable fetus: in 26 animals treated with any of the above compounds, only five showed implantations, and of the total of 48 sites, not a single viable fetus was observed.

Similar results was observed when the above dose is decreased to 1 $\mu$g per injection or increased to 20 $\mu$g, i.e., a range of 5-100 $\mu$g/kg of body weight.

EXAMPLE 3

When a compound of the above formula is administered to immature female rats, uterine and ovarian development is prevented with the result that ovaries and uteri remain in a pre-puberal state as long as the treatment is continued. Upon discontinuation of the administration of any of the above compounds, normal development of the organs resumes with the animals attaining complete maturity 2-3 weeks later.

EXAMPLE 4

Pregnant rabbits were given single subcutaneous injections of 12.5 $\mu$g/kg of the compounds used in Example 2 by the route and vehicle shown there on day 14 of gestation. While in a control animal (receiving only the above vehicle), 7 of 8 implants were found viable, the animals injected with Compounds A, B and C showed only an average of one viable fetus per 7 implants. In all instances, the animals were sacrificed on day 28 of gestation.

As shown above, the treatment with Compounds A, B or C in small amounts at almost any time during the female cycle has a profound effect on fertility or reproduction. In most instances, single doses of 2 – 100 $\mu$g/kg of body weight are sufficient, but it may be desirable to administer the above nonapeptide daily for several days depending on the length of cycle of the particular animal involved.

In the case of humans, oral administration is preferred for reasons of simplicity. Daily doses of 0.02 – 10mg/kg for several days following menses or after ovulation will prevent pregnancy. Tablets containing 5 to 100 mg represent a particularly suitable dosage unit range. Tablets of this type are prepared in the usual fashion by compounding the active ingredient with starch, granulating the mixture and, after adding the necessary fillers, flavoring agents, lubricants, etc., the mixture is slugged and passed through a 30-mesh screen. The thoroughly blended mixture is then compressed into tablets of desired hardness with the usual punch, preferably to make bisected tablets for easier b.i.d. administration.

In animals, subcutaneous administration may be more desirable. In this instance, the active ingredient is dissolved in physiologically acceptable saline optionally containing 0.05 – 1% by weight of serum albumin at a concentration of between 0.5 and 10% by weight of the above compound for injection in order to prevent pregnancies or, if desired, to synchronize a herd or flock of animals.

The demonstrated effects on the animals' reproductive cycle by the compounds of this invention are primarily based on the imbalance of steroid hormones caused therewith in the reproductive organs of the animals treated. This can be demonstrated by administering exogenous estrogens to the animals treated in the above fashion. More specifically, if estradiol is subcutaneously given to rats treated with Compounds A, B or C (days 2 – 6 of gestation) on days 4 and 5 of gestation at a dose of as little as 0.1 $\mu$g each (dissolved in sesame oil), implantation will take place in 3 of 8 animals, producing substantially only viable embryos. The process of this invention can therefore be summarized as being a process of preventing the proper balance of steroids in the reproductive organs, thereby causing the demonstrated inability to reproduce.

The process of the current invention thus can be used to prevent ovulation in immature animals in order to postpone their entering the reproductive cycle; it can be used to delay the maturation of ova and thus synchronize a herd, flock, drove, pack or other aggregations of animals; it can be used after ovulation to prevent implantation. In either case, reproduction is prevented. The new process can also be used to prevent fertilization by inducing premature ovulation and can be used to inhibit implantation of the ova before it is attached to the uterus or thereafter to cause abortive action on the embryo. The higher dosage level discussed above is required solely for oral administration, because only a relatively small portion thereof effectively enters the blood stream. The lower dosage levels are suitable for all parenteral administrations, and the above compounds are particularly well suited for use in suppositories or for intravaginal administration.

What is claimed is:

1. A process for preventing reproduction consisting essentially in administering to a female, warm-blooded animal in or before reaching the reproductive age, an effective dose of the nonapeptide L-pGlu-L-His-L-Trp-L-Ser-L-Tyr-X-L-Leu-L-Arg-L-Pro-NH-$C_2H_5$ wherein X denotes the divalent, optically active D-form of tryptophane, tyrosine or phenylanine for at least one day in the period before said female produced one or more mature ova or after ovulation occurred.

2. The process of claim 1 wherein X in said nonapeptide is D-tryptophane.

3. The process of claim 1 wherein X is D-phenylalanine.

4. The process of claim 1 wherein X is D-tyrosine.

5. The process of claim 1 wherein said nonapeptide is given as a single parenteral dose of between 1 and 500 $\mu g/kg$.

6. The process of claim 1 wherein said dose is administered orally at a dose of between 0.02 and 10 mg/kg.

7. An oral composition for preventing reproduction in warm-blooded female animals containing between 5 and 100 mg of the nonapeptide L-pGlu-L-His-L-Trp-L-Ser-L-Tyr-X-L-Leu-L-Arg-L-Pro-NH-$C_2H_5$ wherein X denotes the divalent, optically active D-form of tryptophane, tyrosine or phenyl-alanine together with a pharmaceutically acceptable carrier.

* * * * *